United States Patent [19]

Kunz et al.

[11] Patent Number: 5,324,786

[45] Date of Patent: * Jun. 28, 1994

[54] PROCESS FOR PREPARATION OF A SOLID PHASE SYSTEM

[75] Inventors: Horst Kunz, Mainz; Winfried Kosch, Wiesbaden; Joachim März, Mainz-Zahlbach, all of Fed. Rep. of Germany

[73] Assignee: Orpegen Medizinische-Molekular Biologische Forschungsgesellschaft mbh, Heidelberg, Fed. Rep. of Germany

[*] Notice: The portion of the term of this patent subsequent to May 29, 2007 has been disclaimed.

[21] Appl. No.: 695,424

[22] Filed: May 3, 1991

Related U.S. Application Data

[62] Division of Ser. No. 576,366, Aug. 31, 1990, Pat. No. 5,214,195.

[30] Foreign Application Priority Data

Aug. 31, 1989 [DE] Fed. Rep. of Germany ....... 3928909
Nov. 23, 1989 [DE] Fed. Rep. of Germany ....... 3938850

[51] Int. Cl.$^5$ .......................................... C08F 257/02
[52] U.S. Cl. ................... 525/302; 525/288; 525/291; 525/293; 525/296; 525/303; 525/54.11
[58] Field of Search ............... 525/288, 291, 293, 296, 525/302, 303, 54.11

[56] References Cited

U.S. PATENT DOCUMENTS

4,929,671  5/1990  Kunz et al. ...................... 525/54.11
5,124,448  6/1992  Tschaen et al. .................. 540/310

FOREIGN PATENT DOCUMENTS

0295540  12/1988  European Pat. Off. .
2154439  5/1973  Fed. Rep. of Germany .

OTHER PUBLICATIONS

Chemical Abstracts, vol. 109, No. 7, 55223x (Aug. 1988).
Lambat et al. "Esters and Amides from Aziridine 2-Carboxylic Acid Salts", Tetrahedron Letters, vol. 26, No. 42 (1985) pp. 4439–4442.

*Primary Examiner*—Vasu S. Jagannathan
*Attorney, Agent, or Firm*—Felfe & Lynch

[57] ABSTRACT

The invention provides a method for the production of a solid phase system of the formula $F-(-R^3-Y-CO-CR^2=CR^1-CH_2-X)_m$ using new allyl esters of the formula:

$$X-CH_2-CR^1=CR^2-CO-Y-R^3-A \qquad (I).$$

$R^1$ and $R^2$ are hydrogen, halogen, alkyl or aryl, $R^3$ is a spacer, X is acyloxy where acyl is the residue of an aliphatic carboxylic acid or is RCO— in which R is an organic group. Y is oxygen or sulphur or an —NH— group and A is a grouping which can react with a solid carrier material F, which contains functional groups B. A and B are groups which react with one another with condensation and/or addition and formation of a linkage between the solid carrier material and $X-CH_2-CR^1=CR^2-CO-Y-R^3-$.

6 Claims, 3 Drawing Sheets

PROCESS FOR PREPARATION OF A SOLID PHASE SYSTEM

This is a divisional application of application Ser. No. 07/576,366, filed Aug. 31, 1990, and now U.S. Pat. No. 5,214,195.

The present invention is concerned with new allyl esters, processes for the preparation thereof and the use thereof for the synthesis of solid phase systems for solid phase reactions and especially for the solid phase synthesis of peptides, glycopeptides and proteins.

Having regard to the increasing requirements for pharmaceuticals, foodstuff additives and other active materials with regard to the selectivity of the action, the compatibility and the biological degradability, the precision synthesis of peptides is again of great importance. In spite of the now highly developed genetechnological techniques, this also applies to the chemical synthesis of peptides by which alone, for example, peptides with non-natural constructional units and structural elements are accessible.

For the chemical synthesis of peptides, the introduction of the solid phase synthesis according to R. B. Merrifield (see R. B. Merrifield, J.A.C.S., 85, 2149/1963) signifies a great advance. This applies in spite of the problems which have, in the meantime, been recognized which occur ever again in the case of these solid phase peptide syntheses with regard to the purity of the synthesised products.

In the solid phase syntheses, as C-terminal protective and anchor groups there serve benzyl esters which permit the splitting off of the built-up peptides from the polymeric carrier under more or less strongly acidic conditions. The acidic splitting off conditions—in the classical Merrifield synthesis use was made of hydrogen bromide in various solvents or hydrogen fluoride—have the disadvantage that undesired side reactions, such transpeptidisations or transalkylations, can thereby occur. The synthesis of glycopeptides can scarcely be carried out in this way because the sensitive glycosidic bonds of these molecules are cleaved or anomerised under acidic conditions (with regard to the prior art of glycopeptide synthesis, cf. for example, H. Kunz, Angewandte Chemie, 99/1987; Angewandte Chemie, Int. Engl. Ed., 26, 294/1987).

It is an object of the present invention to provide solid phase systems, especially for the solid phase synthesis of peptides and glycopeptides, in the case of which the peptides and glycopeptides can be split off from the polymeric carrier selectively and under such conditions that no cleavage of the glycosidic bonds and no anomerisations take place.

From published Federal Republic of Germany Patent Specification No. 38 03 545, there is known an allylic side chain-containing solid phase system in which the allylic side chains are bound to a solid carrier material. The C-terminal protective (anchor) groups used in these solid phase systems, via which the amino acids and peptides, glycopeptides and the like can be bound to the polymeric carrier, belong to the allyl ester type. Allyl esters can, as C-terminal protective groups in glycopeptide, nucleotide and peptide syntheses, be split off selectively and under mild, almost neutral conditions from the blocked compounds (cf. H. Kunz, Angew. Chemie, 99, 297/1987). This is achieved by noble metal catalysis, for example by catalysis with compounds of the platinum metal group, such as ruthenium, rhodium, palladium, osmium, iridium and platinum, and especially by catalysis with rhodium (I) compounds (cf. H. Waldmann, H. Kunz, Liebigs Ann. Chem., 1983, 1712) or with reactions catalysed by palladium (O) compounds (H. Kunz, H. Waldmann, Angew. Chemie, 96, 47/1984; Angew. Chemie Int. Engl. Ed., 23, 71/1984; H. Kunz and C. Unverzagt, Angew. Chemie, 96, 426/1984; Angew. Chemie, Int. Engl. Ed., 23, 436/1984). By the transfer of the deblocking method to the solid phase peptide synthesis, it is achieved that the removal of the peptide, glycopeptide or nucleotide chain built up on the carrier is possible practically under neutral conditions.

We have now found that allylic side chain-containing solid phase systems, such as are described in published Federal Republic of Germany Patent Specification No. 38 03 545, can also be built up when a conjugate with an N-protected amino acid is first prepared in solution which, on its carboxyl function, carries the allylic principle and this conjugate is then elongated with a spacer grouping which terminates with a functional group for anchoring on to a solid carrier. These "triple constructions" (as it were "preformed terminal handles"), which can be synthesised conventionally and in a simple way in solution, which are analytically exactly definable compounds, can now be connected with the solid carrier with the formation of a solid phase system of the type described in published Federal Republic of Germany Patent Specification No. 38 03 545.

Thus, according to the present invention, there are provided new allyl esters of the general formula:

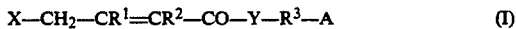

$$X-CH_2-CR^1=CR^2-CO-Y-R^3-A \qquad (I)$$

wherein $R^1$ and $R^2$, which can be the same or different, are hydrogen or halogen atoms or alkyl or aryl radicals, $R^3$ is a linking grouping (spacer), X is an acyloxy group, whereby acyl in the acyloxy radical is the residue of a carboxylic acid or a radical RCO—, in which R is an organic radical, Y is an oxygen or sulphur atom or, especially, an —NH— group and A is a grouping which can react with a solid carrier material F, which contains appropriate functional groups B, either after selective deblocking or directly with the atom grouping B with condensation and/or addition and formation of a linkage between the solid carrier material and the radical $X-CH_2-CR^1=CR^2-CO-Y-R^3-$.

Preferred compounds of general formula (I) are those in which the acyl radical RCO— is a protected or unprotected residue of an amino acid, peptide, glycopeptide, nucleotide, hydroxycarboxylic acid, dicarboxylic acid or tricarboxylic acid, the acyl radical more preferably being the residue of an N-protected amino acid.

Preferred allyl esters of general formula (I) are also those in which $R^1$ and $R^2$ are hydrogen atoms.

Also preferred are compounds of general formula I, wherein the grouping —$R^3$—A, besides the intact grouping X, is a selectively deblockable carboxylic acid ester grouping, for example —CH$_2$—CH$_2$—COO—CH$_2$—CH$_2$—Br, of the radical —CH$_2$—CH$_2$—COOH.

The alkyl radicals $R^1$ and $R^2$ can be straight-chained or branched, the alkyl radicals preferably containing up to 7 and more preferably up to 3 carbon atoms.

An aryl radical $R^1$ or $R^2$ is preferably an unsubstituted or substituted mono- or dicyclic aryl radical, for example a naphthyl-1 or -2 radical or especially a phenyl radical. The aryl radical can contain one or more substituents, for example lower alkyl radicals and/or halogen atoms, but is preferably unsubstituted. Two alkyl substituents can, together with the aryl radical, also form a system of two or more rings, for example tetrahydronaphthalene.

The radical $R^3$ is a linking group (spacer or linker) and can be, for example, one of the spacer groupings previously used in the solid phase technique (Merrifield technique) (for example CASET or CAMET; cf. Römpps Chemie-Lexikon, 8th edition, page 2543). The nature of the group $R^3$ thereby depends especially also upon the process, described hereinafter in more detail, for the preparation of the solid phase systems of the general formula (II) and especially upon the nature of the carrier material and upon the functional groups A and B present on the carrier material and in the compounds of general formula (I). The group $R^3$ can be, for example, an alkylene, aralkylene or arylene radical in which one or more —$CH_2$— groups can be substituted and/or replaced by heteroatoms. $R^3$ is preferably the grouping —$(CH_2)_n$—COO—$CH_2$—$CH_2$— or —$(CH_2)_n$—, wherein n is at least 2, more preferably 2 to 10 and most preferably 2 to 5.

In an acyloxy radical X, in which acyl is the residue of an aliphatic carboxylic acid, acyl is preferably the acid residue of an aliphatic carboxylic acid containing up to 7 and preferably up to 4 carbon atoms, for example a formyl, acetyl or propionyl radical.

An acyl radical RCO— is preferably the unprotected and more preferably the protected residue of an amino acid, of a peptide, glycopeptide, nucleotide, hydroxycarboxylic acid, dicarboxylic acid or tricarboxylic acid and, in particular, is the residue of an N-protected amino acid.

In the compounds of general formula (I), A is preferably a carboxylic acid ester group which, in the presence of the intact amino protective group, can be split into X or RCO—, for example a methyl ester, tert.-butyl ester, 2-haloethyl ester, allyl ester, fluorenyl-9-methyl ester or an active ester or is itself of carboxyl group. Thus, in general formula (I), the $R^3$—A— grouping is preferably, for example, —$CH_2$—$CH_2$—COO—$CH_2$—$CH_2$—Br or —$CH_2$—$CH_2$—COOH.

For the solid carrier material, it is preferable to start from one which contains functional groups B which are well suited for the reaction with the residues A of the compounds of general formula (I).

The carrier material is preferably an organic or inorganic polymer, for example a synthetic, semisynthetic or natural polymer. Such polymers include, for example, cross-linked polyacrylamides, methacrylates, dextrans (for example Sephadex$^R$), cellulose and, in particular, polystyrene. However, the carrier material can also consist of a solid base material which is coated with a material appropriate for the linkage with the allyl side chains, for example is coated with an appropriate polymer or a cross-linked protein. The base material can be, for example, glass, silica gel or also a synthetic resin. Organic polymers for the carrier material and suitable as coatings include, for example, polyacrylamides, polyethylene glycols and especially polystyrenes. As solid, functional group B-containing carrier material, there is particularly used an aminomethylated polystyrene.

The residues A and B are those groupings which react either directly or after selective deblocking with condensation and/or addition and formation of a linkage between the carrier material and the radical X—$CH_2$—$CR^1$=$CR^2$—CO—Y—$R^3$—. Such groups are preferably those usually employed in condensation and addition reactions, for example amino groups such as in the form of an aminomethyl radical on the solid carrier, halogen atoms, ester groupings, carboxyl groups, nitrile groups and the like. As a rule, the condensation and/or addition reactions can be carried out in known manner, for example with the splitting off of water, halogen, hydrogen or the like. The residue A is preferably a halogen atom or a carboxyl group.

Halogen is preferably fluorine, chlorine, bromine or iodine. It is preferably chlorine or bromine and, in the meaning of A, is especially bromine.

In a preferred embodiment for the build up the solid phase system, for example an aminomethyl radical (group B)-containing polystyrene is reacted with a compound of general formula (I) and especially with a compound of general formula (I) in which $R^3$—A— is the grouping —$CH_2$—$CH_2$—COOH which is produced from an appropriate selectively-cleavable ester, for example —$CH_2$—$CH_2$—COO—$CH_2$—$CH_2Br$.

The present invention also provides a process for the preparation of the compounds of general formula (I) according to the present invention, wherein
a) a compound of the general formula:

$$BrCH_2—CR^1=CR^2—COOCH_2CCl_3 \quad (2)$$

in which $R^1$ and $R^2$ have the above-given meanings, is reacted with a salt of an acid of the general formula XH (1), in which X has the above-given meaning, the so-obtained trichloroethyl ester of the general formula:

$$X—CH_2—CR^1=CR^2—COOCH_2CCl_3 \quad (3)$$

in which $R^1$, $R^2$ and X have the above-given meanings, is converted into the free acid of the general formula:

$$X—CH_2—CR^1=CR^2—COOH \quad (4)$$

in which $R^1$, $R^2$ and X have the above-given meanings, and this is reacted with a compound of the general formula:

$$HY—R^3—A \quad (5)$$

in which A, $R^3$ and Y have the above-given meanings, to give a compound of general formula (I); or
b) a compound of the general formula:

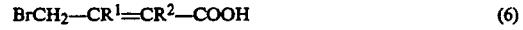

$$BrCH_2—CR^1=CR^2—COOH \quad (6)$$

in which $R^1$ and $R^2$ have the above-given meanings, is reacted with a compound of general formula (5) to give a compound of the general formula:

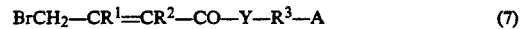

$$BrCH_2—CR^1=CR^2—CO—Y—R^3—A \quad (7)$$

in which A, $R^1$, $R^2$ and Y have the above-given meanings, and this compound is then converted into a compound of general formula (I) by reaction with a salt of an acid of general formula XH (1), in which X has the above-given meaning; or
c) a compound of the general formula (6) is reacted with a compound of the general formula:

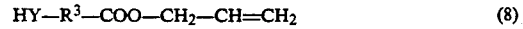

$$HY—R^3—COO—CH_2—CH=CH_2 \quad (8)$$

in which $R^3$ and Y have the above-given meanings, to give a compound of the general formula:

$$BrCH_2-CR^1=CR^2-CO-Y-R^3-COO-CH_2-CH=CH_2 \quad (9)$$

in which $R^1$, $R^2$, $R^3$ and Y have the above-given meanings, this compound is then reacted with the salt of an acid of the general formula XH (1), in which X has the above-given meaning, to give a compound of the general formula:

$$X-CH_2-CR^1=CR^2-CO-Y-R^3-COO-CH_2-CH=CH_2 \quad (10)$$

in which $R^1$, $R^2$, $R^3$, X and Y have the above-given meanings, and, by splitting off of the allyl ester group, this compound is converted into a compound of the general formula (I), wherein A is a carboxyl group, and, if desired, in a compound of general formula (I), a radical A is converted into another radical A within the above-given definition of A.

The acid XH is preferably an N-protected amino acid and the salt thereof is preferably a caesium salt.

The conditions for the individual, known reaction steps (temperature, solvent, period of reaction, etc.) correspond to the conditions usual for such reactions. The reaction conditions which are most favourable for individual cases can easily be determined and, as a rule, lie within the range of the reactions described in connection with FIGS. 1 to 3 of the accompanying drawings and within the reaction conditions given in the following Examples.

FIGS. 1 to 3 of the accompanying drawings show the process according to the present invention for the preparation of compounds of general formula (I) using the example of representative compounds.

Figure 1:
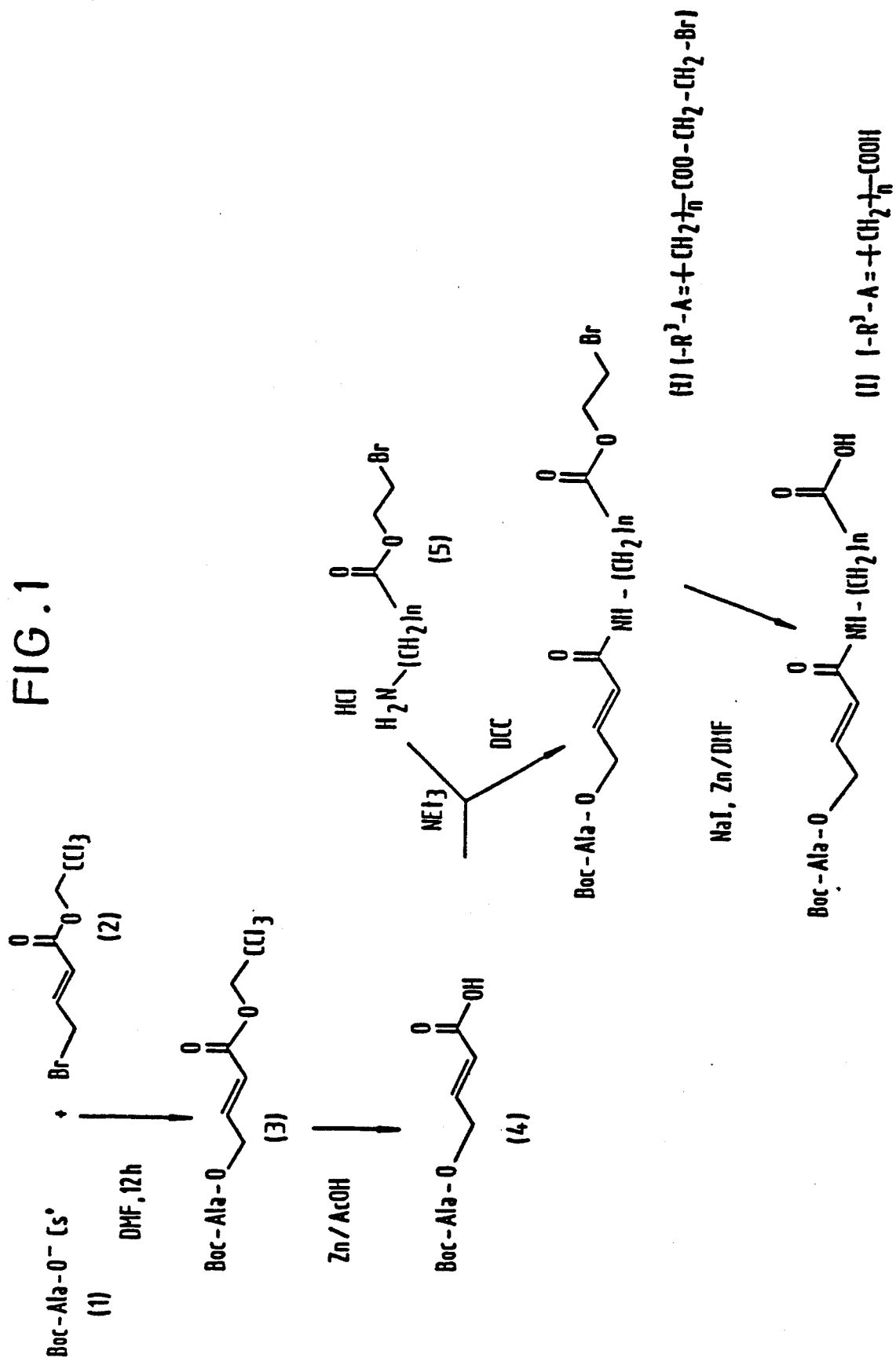
FIG. 1 shows the course of the reaction according to process variant a)

According to process variant a) (FIG. 1), a salt of a compound HX is reacted with compound (2) in dimethylformamide, while stirring. The compound (3) obtained is dissolved in glacial acetic acid and converted in the presence of the threefold amount of zinc into the compound (4). The coupling of (4) with (5) (in the form of the hydrochloride) takes place by reacting a solution of (5) in methylene chloride/triethylamine or Hünig base with (4) in the presence N,N'-dicyclohexylcarbodiimide (DCC) and 1-hydroxybenzotriazole (HOBt) or also with the use of 2-ethoxy-1-ethoxycarbonyl-1,2-dihydroquinoline (EEDQ). The conversion (ester cleavage) of the compound (I)(in which $-R^3-A$ is the radical $-(CH_2)_n-COO-CH_2-CH_2Br$) into the compound (I)(in which $-R^3-A$ is the radical $-(CH_2)_n-COOH$) can take place in dimethylformamide in the presence of zinc/sodium iodide.

Figure 2:
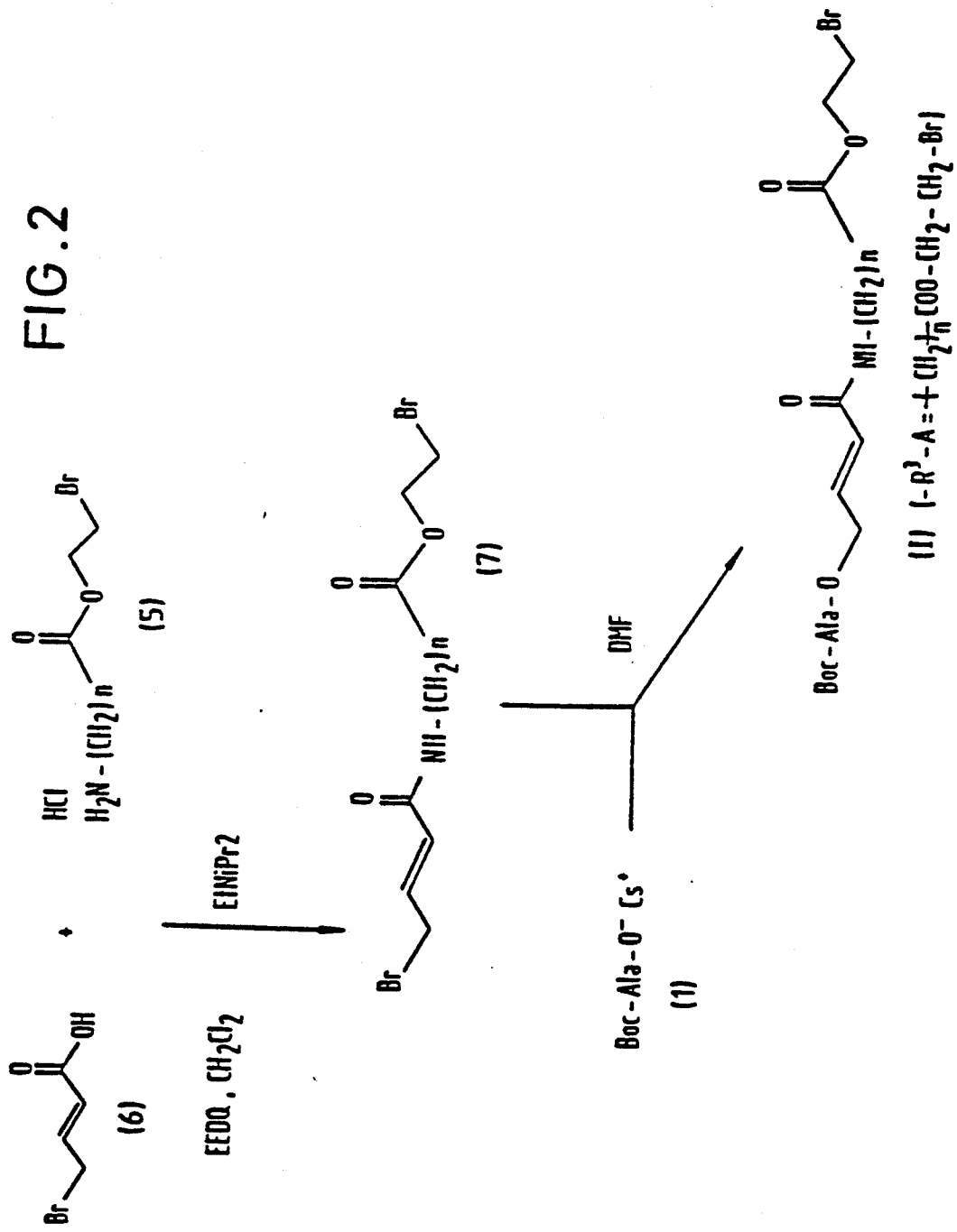
FIG. 2 shows the course of the reaction according to process variant b)

According to process variant b)(FIG. 2), the coupling of (6) with (5) to give (7) can take place analogously to the coupling of (4) with (5) described above under a), for example with DCC and EEDQ as coupling reagent. The reaction of (7) with the salt of the acid HX to give a compound of general formula (I) takes place analogously to the reaction of the salt of the acid HX with (2) described for process variant a).

Figure 3:
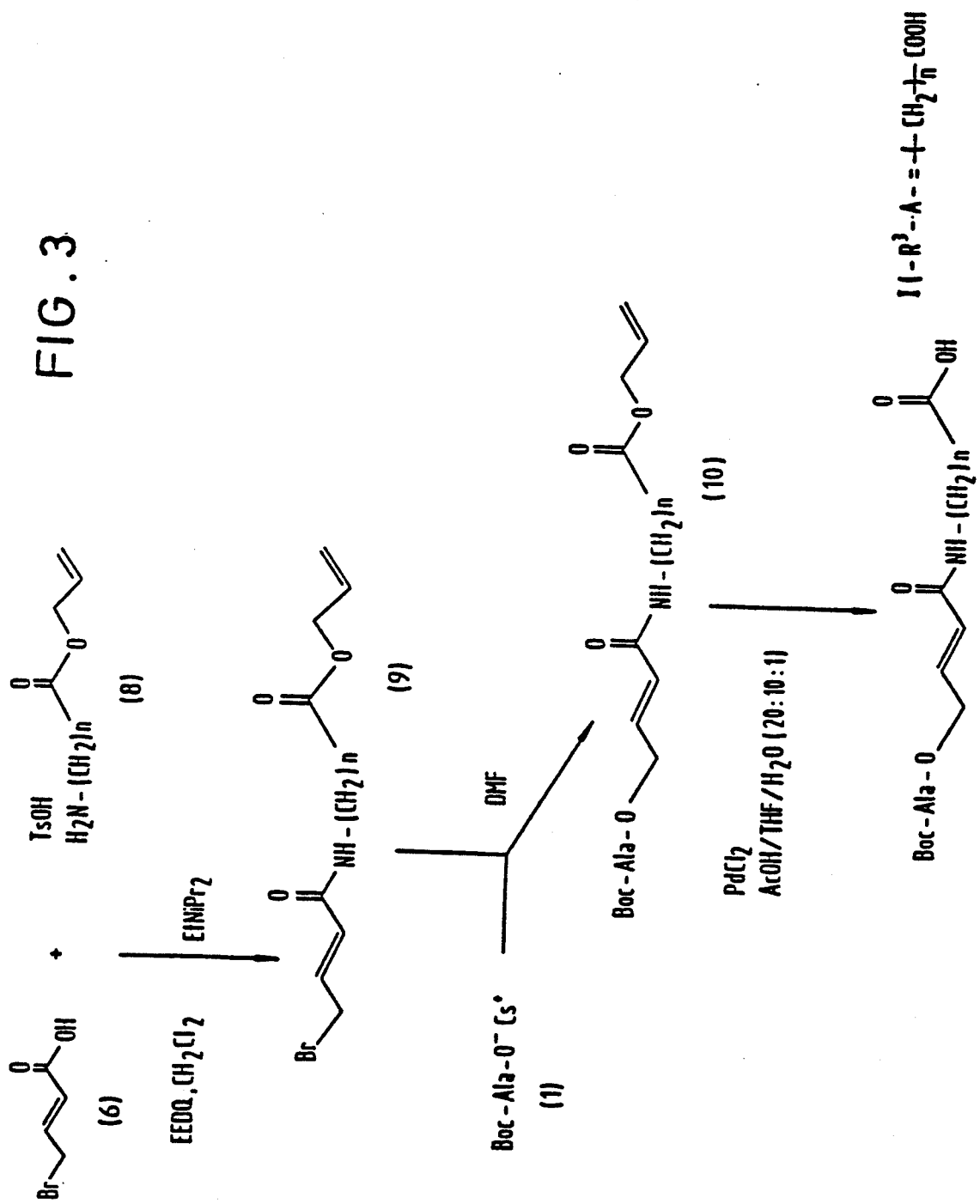
FIG. 3 shows the course of the reaction according to process variant c).

According to process variant c)(FIG. 3), the coupling of (8) with (6) to give (9) takes place analogously to the corresponding reactions in process variant a) or b), for example with EEDQ as coupling reagent. The reaction of (9) with the salt of the acid HX also takes place analogously to the corresponding reaction step in process variant a) or b). The cleavage of the ester (10) to give a compound of general formula (I) takes place, for example, in glacial acetic acid/tetrahydrofuran/water (20:20:1 v/v/v) with palladium chloride.

For the preparation of the compounds of general formula (I), as acid HX there is preferably used an N-protected amino acid and, as salt, the caesium salt is preferred.

As protective groups, there can be used the conventionally employed protective groups, for example Z (Cbo, Cbz), Boc, Ddz, Trt, Bpoc (Dpoc), OBut, Obzl, Nps, Fmoc, Msoc, Mch, Dcboc (with regard to the abbreviations, cf. for example Eur. J. Biochem., 74, 1-6/1977).

The present invention is also concerned with the use of a compound of general formula (I) according to the present invention for the build-up of a solid phase system of the general formula:

$$F-(R^3-Y-CO-CR^2=CR^1-CH_2-X)_m \quad (II)$$

wherein F indicates a solid carrier material, $R^1$, $R^2$, $R^3$, Y and X have the above-given meanings and m is the number of side chains bound to the carrier material; especially for use in solid phase reactions and, above all, for the solid phase syntheses of peptides, glycopeptides, nucleotides and proteins.

The solid phase systems of general formula (II) correspond to the solid phase systems described in published Federal Republic of Germany Patent Specification No. 38 03 545. Because of their allylic side chain, these solid phase systems are suitable for the solid phase synthesis of peptides and glycopeptides in which the peptides and glycopeptides can be split selectively from the polymeric carrier and under such mild conditions that no cleavage of the glycosidic bonds and no anomerisations take place.

The splitting off in the presence of catalytic amounts of a compound of the platinum group of metals, preferably in the presence of a rhodium (I) compound and especially in the presence of a palladium (O) compound, can be carried out in a solvent or solvent system appropriate for this purpose, for example in tetrahydrofuran, in the presence of a nucleophilic compound, for example morpholine, dimedone or another easily deprotonisable CH-acidic compound. The reaction is preferably carried out at ambient temperature and is carried out with the exclusion of oxygen.

Because of the extraordinarily mild conditions of splitting off, with the solid phase systems according to the present invention, it is possible to carry out the splitting off of the peptides, glycopeptides, nucleotides and other radicals selectively and without cleavage of glycosidic bonds or of anomerisations or isomerisations.

The present invention also provides a process for the preparation of a solid phase system of the above-given general formula (II), wherein a compound of general formula (I) according to the present invention is reacted with a solid carrier material F, which contains appropriate functional groups B, and wherein A and B signify atom groupings which react with one another with condensation and/or addition and formation of a linkage between the solid carrier material and the radical X—CH$_2$—CR$^1$=CR$^2$—CO—Y—R$^3$—.

The solid carrier material is preferably an organic or inorganic polymer or also a solid base material which is coated with a material suitable for linking with the compounds of general formula (I). As polymer or as material suitable for linking with compounds of general formula (I), there is especially preferably used cross-linked polystyrene. In particular, the solid, functional group B-containing carrier materials is an aminomethylated polystyrene.

The following Examples are given for the purpose of illustrating the present invention, the following abbreviations thereby being used:
As=amino acid
DCC=N,N'-dicyclohexylcarbodiimide
DIIC=N,N'-diisopropylcarbodiimide
EEDQ=2-ethoxy-1-ethoxycarbonyl-1,2-dihydroquinoline,
HOBt=1-hydroxybenzotriazole
SG=protective group.

EXAMPLE 1

Crotonic acid 2,2,2-trichloroethyl ester (i)

In 200 ml. carbon tetrachloride are dissolved 0.5 mole (43.07 g.) crotonic acid and the equimolar amount of 2,2,2-trichloroethanol, 1 ml. concentrated sulphuric acid is added thereto and the reaction mixture is heated under reflux on a water separator until the theoretical amount of water (9 ml.) has separated off. Subsequently, the organic phase is shaken out twice with, in each case, 100 ml. aqueous 2N sodium hydrogen carbonate solution and twice with, in each case, 50 ml. of water, the organic phase is then dried with anhydrous magnesium sulphate and the solvent is distilled off in a vacuum. There is finally obtained the desired product (i) in the form of a bright yellow oil in a yield of 95% of theory. C$_6$H$_7$O$_2$Cl$_3$ (217.4791)

Elementary analysis calc.: C 33.13%; H 3.24%; Cl 48.90%; found: 32.97%; 3.43%; 48.82%; Rf value: 0.57 (PE/EE: 20:1 v/v).

200 MHz $^1$H-NMR (CDCl$_3$): 7.25–7.03, 1H, m, CH=, J$_{trans}$=15.6, J$_{cis}$=10.6, J=1.6 Hz; 5.98–5.88, 1H, m, CH=, J=7 Hz; 4.76, 2H, s, CH$_2$; 1.91, dd, 3H, CH$_3$.

50 MHz $^{13}$C-NMR (CDCl$_3$): 164.55; C=O; 147.51; 121.25; CH=CH; 95.17; CCl$_3$; 73.84; CH$_2$; 18.26; CH$_3$.

EXAMPLE 2

4-Bromocrotonic acid 2,2,2-trichloroethyl ester (ii)

The bromination reaction takes place in carbon tetrachloride with N-bromosuccinimide and AIBN as radical former. For this purpose, an equimolar amount of ester (i) and 0.45 mole N-bromosuccinimide are mixed with 300 ml. carbon tetrachloride and a spatula tip of AIBN added thereto. The reaction mixture is heated under reflux for 4 hours, subsequently allowed to cool and the precipitated succinimide (0.41 mole; 92% of theory) is filtered off. After distilling off the solvent in a vacuum, the residue is purified by column chromatography using PE/EE (25:1 v/v) as elution agent. The end product obtained is a yellow oil. The yield of 75% of theory. C$_6$H$_6$O$_2$BrCl$_3$ (296.3752 g./mole).

Elementary analysis calc.: C 24.31%; H 2.04%; Br 26.96%; Cl 35.88%; found: 24.61%; 1.99%; 26.75%; 35.54%.

Rf value MHz $^1$H-NMR (CDCl$_3$): 7.25–7.06, 1H, m, CH=, J$_{trans}$=15.3 Hz, J$_{cis}$=7.3, J=6.3 Hz; 6.18–6.09, 1H, m, CH=; 4.79, 2H, s, CH$_2$; 4.03, dd, 3H, CH$_2$.

50 MHz $^{13}$C-NMR (CDCl$_3$): 160.95; C=O; 141.48; 120.37; CH=CH; 92.17, CCl$_3$; 71.53; CH$_2$; 25.88; CH$_2$Br.

EXAMPLE 3

N-tert.-butyloxycarbonylalanyloxycrotonic acid 2,2,2-trichloroethyl ester (iii)

As precursor of this reaction, there first takes place the preparation of the caesium salt of the amino acid. For this purpose, 1.89 g. (0.01 mole) of Bocalanine is dissolved in 10 ml. methanol and mixed with 5 mmole caesium carbonate. With the evolution of carbon dioxide, there is formed the caesium salt which, after removal of the solvent by distillation in a vacuum, is dissolved in dimethylformamide. 0.011 mole of (ii) is now added thereto and the reaction mixture is stirred for 12 hours. Subsequently, precipitated caesium bromide is filtered off and the dimethylformamide is distilled off in a vacuum. The crude product is purified by column chromatography using, as elution agent, PE/EE (4:1 v/v). Yellowish crystals are obtained. C$_{14}$H$_{20}$O$_6$NCl$_3$ (404.6741 g./mole)

Elementary analysis calc.: C 41.55%; H 4.98%; N 3.46%; Cl 26.28%; found: 41.84%; 4.82%; 3.31%; 26.38%; Rf value: 0.42 (PE/EE 4:1 v/v). Melting point: 58° C. [α]$_D^{22}$=−21.26 (c=1, methanol)

200 MHz $^1$H-NMR (CDCl$_3$): 7.15–6.99, 1H, m, CH=, J$_{trans}$=15.5 Hz, J$_{cis}$=7.5, J=4.3 Hz; 6.16–6.08, 1H, m, CH=; 5.07, 1H, d, NH, J=6.3 Hz; 4.77, 2H, s, CH$_2$-ester; 4.88–4.72, 2H, m, CH$_2$-crot., 4.37, 1H, dd, CH-Ala, J=7.1 Hz, 1.51–1.37, 12H, m, 4×CH$_3$.

50 MHz $^{13}$C-NMR (CDCl$_3$): 172.66; 163.78; 155.03; C=O; 143.22; 120.71; CH=CH; 94.87; CCl$_3$; 80.08; C$_q$-Boc, 74.12; CH$_2$; 62.99; CH$_2$-croton; 49.35; CH-Ala; 28.30; CH$_3$-Boc; 18.34; CH$_3$-Ala.

EXAMPLE 4

N-tert.-Butyloxycarbonylalanyloxycrotonic acid (iv)

(cf. B. Marinier et al., Can. J. Chem., 51, 208–214/1973)

1.2 g. (2.96 mmole) of the ester from Example 3 is dissolved in 50 ml. glacial acetic acid and mixed with the threefold molar amount of zinc (9.17 mmole; 0.6 g.; previously activated with 1N hydrochloric acid). The reaction mixture is stirred for 2 hours and the acetic acid subsequently removed by distilling off in a vacuum. The residue is now taken up in 50 ml. each of chloroform and saturated sodium hydrogen carbonate solution and filtered over a little kieselguhr. The organic phase is then extracted several times with 20 ml. amounts of sodium hydrogen carbonate solution. The combined aqueous alkaline phases are covered with ethyl acetate and carefully acidified with dilute hydrochloric acid to pH 2. Extraction is carried out three times with, in each case, 30 ml. ethyl acetate, the combined organic phases are dried with anhydrous magnesium sulphate and the solvent is removed by distillation in a vacuum. If necessary, the product is further purified by means of column chromatography (elution agent PE/EE 1:1 v/v). Finally, there are obtained colourless crystals of (iv) in quantitative yield. $C_{12}H_{19}O_6N$ (273.2852).

ELEMENTARY ANALYSIS calc.: C 52.74%; H 7.00%; N 5.12%; found: 52.65%; 7.23%; 4.89%; Rf value: 0.21 (PE/EE 2:1 v/v); melting point: 65° C. $[\alpha]_D^{22} = -36.12$ (c=1, methanol)

200 MHz $^1$H-NMR (CDCl$_3$); 7.25–6.93, 1H, m, CH=, $J_{trans}$=15.7 hz, $J_{cis}$=9.7, J=2.2 Hz; 6.06–5.98, 1H, m, CH=; 5.12, 1H, d, NH, J=7.3 Hz; 4.78–6.06–5.98, 1H, m, CH=; 5.12, 1H, d, NH, J=7.3 Hz; 4.78–4.72, 2H, m, CH$_2$-crot., 4.37, 1H, dd, CH-Ala, J=7.3 Hz; 1.50–1.23, 12H, m, 4×CH$_3$.

50 MHz $^{13}$C-NMR (CDCl$_3$): 172.68; 169.89; 155.03; C=O; 142.66; 121.91; CH=CH; 80.08; C$_q$-Boc, 63.08; CH$_2$; 49.29; CH-Ala, 28.27; CH$_3$-Boc; 18.33; CH$_3$-Ala.

EXAMPLE 5

Preparation of amino acid 2-bromoethyl ester hydrochlorides (cf. H. Kunz, M. Buchholz, Chem. Ber., 112, 2145/1979)

0.2 mole of the amino acid is slurried, with stirring, in about 150 ml. freshly distilled 2-bromoethanol and cooled to −10° C. 30 g. (0.25 mole) distilled thionyl chloride are slowly added dropwise thereto, the reaction mixture is allowed to come to ambient temperature and the reaction mixture is stirred until a completely clear solution is obtained. The clear solution is slowly added dropwise, while stirring, into about 1 liter of diethyl ether/petroleum ether (2:1 v/v). The precipitated crystalline hydrochlorides are filtered off with suction and subsequently washed with the precipitation agent. Excess halohydrin is recovered from the filtrate. All bromoethyl esters can be obtained in a yield greater than 98% of theory.

β-Alanine-2-bromoethyl ester hydrochloride $C_5H_{11}O_2NBrCl$ (232.5044)

Elementary analysis calc.: C 25.83%; H 4.77%; N 6.02%; Br 34.37%; Cl 15.25%; found: 25.76%; 4.55%; 5.98%; 34.52%; 15.14%; Rf value: 0.21 (dichloromethane/methanol 1:1 v/v); melting point: 68° C.

200 MHz $^1$H-NMR (DMSO-d$_6$): 7.99, 3H, s, NH$_3^+$; 4.35, 2H, t, CH$_2$ ester, =5.5 Hz; 3.85, 2H, t, CH$_2$-ester; 3.00, 2H, t, CH$_2$-β-Ala, J=7 Hz; 2.74, 2H, t, CH$_2$-β-Ala.

50 MHz $^{13}$C-NMR (DMSO-d$_6$): 169.83; C=O; 64.33; 42.28; 34.53; 31.21; CH$_2$.

6-Aminocapronic acid 2-bromoethyl ester hydrochloride $C_8H_{17}O_2NBrCl$ (274.5852)

Elementary analysis calc.: C 34.99%; H 6.24%; N 5.10%; Br 29.10%; Cl 12.91%; found: 34.56%; 5.82%; 4.91%; 29.16%; 12.52%.

Rf value $^1$H-NMR (DMSO-d$_6$): 7.94, 3H, s, NH$_3^+$; 4.25, 2H, t, CH$_2$-ester, J=5.5 Hz; 3.79, 2H, t, CH$_2$-ester; 2.74, 2H, m, CH$_2$, J=6.1 Hz; 2.27, m, CH$_2$, J=7.4 Hz; 1.62–1.14, 6H, m, CH$_2$.

50 MHz $^{13}$C-NMR (DMSO-d$_6$): 172.41; C=O, 63.70; 42.53; 35.04; 30.79; 26.39; 25.12; 23.75; CH$_2$.

EXAMPLE 6

N-tert.-Butyloxycarbonylalanyloxy-4-crotonyl-β-alanine 2-bromoethyl ester (v)

9 mmole β-alanine 2-bromoethyl ester hydrochloride (va) (2.09 g.) are dissolved in 100 ml. anhydrous methylene chloride, the equivalent amount of triethylamine (0.91 g.) or of Hünig base are added thereto and the reaction mixture is stirred for 1 hour.

Into this solution are now added 2.46 of (iv) (9 mmole), 2.12 g. DCC (10 mmole) and 2.03 g. HOBt (15 mmole). Already after a few minutes, dicyclohexylurea precipitates out of the reaction. However, for completion of the reaction, stirring is continued for 12 hours. After filtering off the urea derivative and removing the solvent by distillation in a vacuum, the crude product obtained is purified by chromatography, using ethyl acetate as elution agent.

The coupling can also be carried out with the help of EEDQ but the yields always lie between 44 and 59% of theory.

$C_{17}H_{27}O_7N_2Br$ (451.3113)

Elementary analysis calc.: C 45.24%; H 6.03%; N 6.21%; Br 17.70%; found: 45.26%; 6.41%; 6.26%; 17.43%; Rf value: 0.62 (EE).

Melting point: 72°–73° C. $[\alpha]_D^{22} = -19.84$ (c=1, methanol)

200 MHz $^1$H-NMR (CDCl$_3$): 6.78–6.61, 2H, m, NH, CH=, $J_{trans}$=15.4 Hz, $J_{cis}$=9.2 Hz, $J_{NH}$=7.3 Hz; 6.09–5.94, 1H, m, CH=, J=4.3 Hz; 5.18, 1H, d, NH, J=7.7 Hz; 4.69–4.67, 2H, m, CH$_2$-crot.; 4.35–4.23, 3H, m, CH-Ala, J=7.3 Hz, CH$_2$-ester, J=6 Hz; 3.52–3.40, 4H, m, CH$_2$-ester, CH$_2$-β-Ala, J=6.1 Hz; 2.54, 2H, t, CH$_2$-β-Ala; 1.34–1.19, 12H, m, 4×CH$_3$.

50 MHz $^{13}$C-NMR (CDCl$_3$): 172.74; 171.64; 164.88; 155.15; C=O; 136.40; 125.05; CH=CH; 79.97; C$_q$-Boc; 49.39; CH-Ala; 63.92; CH$_2$-croton; 63.44; 35.02, 33.92; 18.25; CH$_2$; 28.28; CH$_3$-Boc; 17.87; CH$_3$-Ala.

EXAMPLE 7

N-tert.-Butyloxycarbonylalanyloxy-4-crotonyl-β-alanine (vi)

The cleavage of the bromoethyl ester takes place analogously to H. Kunz and M. Buchholz (cf. H. Kunz, M. Buchholz, Chem. Ber., 112, 245/1979).

The bromoethyl ester (v)(3.5 mmole; 1.58 g.) is dissolved in 30 ml. dimethylformamide, a spatula tip of sodium iodide is added thereto and the reaction mixture is stirred for 1 hour at 45° C. The threefold molar amount of activated zinc is now added thereto and the reaction mixture is stirred at ambient temperature until the reaction is complete (about 12 hours; TLC monitoring, PE/EE 2:1 v/v). After distilling off the solvent in a vacuum, further working is carried out analogously to that used for compound (iv). For the removal of catalyst residues (iodine), the organic phase is additionally shaken out three times with, in each case, 15 ml. 1N aqueous sodium thiosulphate solution. If, after the shaking out, the compound is still not pure (TLC monitoring), it is purified by column chromatography (methanol/dichloromethane 3:1 v/v). There is finally obtained a bright yellow oil which, in the case of the addition of diethyl ether/petroleum ether, precipitates out in the form of colourless crystals. The yield of this "triple-handled" compound is 75% of theory.

$C_{15}H_{24}O_7N_2$ (344.3652).

Elementary analysis calc.: C 52.31%; H 7.02%; N 8.13%; found: 52.25%; 7.07%; 8.26%; Rf value: 0.22 (EE); 0.66 (methanol/dichloromethane 3:1 v/v).

Melting point: 43°–45° C. $[\alpha]_D^{22} = -15.54$ (c=0.99, methanol)

400 MHz $^1$H-NMR (CDCl$_3$): 10.1, 1H, s, COOH; 6.97, 1H, d, NH-Ala, J=7.3 Hz; 6.97–6.72, 1H, m, CH=, J$_{trans}$=15.4 Hz; 6.05–6.04, 1H, m, CH=, J=4.6 Hz; 5.31, 1H, d, NH, J=7.3 Hz; 4.70–4.69, 2H, m, CH$_2$-crot; 4.26, 1H, dd, CH-Ala, J=7.3 Hz; 3.51, 2H, t, CH$_2$-β-Ala, J=6.1 Hz; 2.53, 2H, t, CH$_2$-β-Ala; 1.39–1.32, 12H, m, 4×CH$_3$.

100 MHz $^{13}$C-NMR (DMSO-d$_6$): 175.35; 172.54; 163.80; 155.17; C=O; 134.91; 125.84; CH=CH; 78.10, C$_q$-Boc; 49.91; CH-Ala; 62.97; CH$_2$-croton.; 36.25; 35.90; CH$_2$; 28.08; CH$_3$-Boc; 16.83; CH$_3$-Ala.

EXAMPLE 8

N-tert.-Butyloxycarbonylalanyloxy-4-crotonyl-6-amidocaproic acid 2-bromoethyl ester (vii)

The preparation of this compound does not take place as described in Example 6 with DCC as coupling reagent but with the help of EEDQ. Otherwise, the batch and course of the reaction are analogous. After column chromatography with PE/EE (2:1 v/v), there is obtained a yellowish oil which, upon the addition of diethyl ether/petroleum ether, crystallises in colourless form. The yield is 69% of theory. $C_{20}H_{33}O_7N_2Br$ (493.3953)

Elementary analysis calc.: C 48.68%; H 6.74%; N 5.67%; Br 16.19%; found: 48.89%; 6.91%; 5.41%; 15.88%; Melting point: 58° C. $[\alpha]_D^{22} = -11.99$ (c=1, methanol)

400 MHz $^1$H-NMR (DMSO-d$_6$): 8.0, 1H, t, NH-capr., J=5.6 Hz; 7.3, 1H, d, NH-Ala, J=7.3 Hz; 6.60–6.53, 1H, m, CH=, J$_{trans}$=15.5 Hz, J$_{cis}$=9.7 Hz, J=1.6 Hz; 6.05–6.03, m, 1H, M, CH=, J=4.8 Hz, 4.75–4.67, 2H, m, CH$_2$-crot.; 4.32, 2H, t, CH$_2$-ester, J=5.7 Hz; 4.05, 1H, dd, CH-Ala, J=7.3 Hz; 3.65, 2H, t, CH$_2$-ester; 3.08, 2H, m, CH$_2$, J=6.1 Hz; J=6.8 Hz; 2.33–2.29, 2H, m, CH$_2$, J=7.4 Hz; 1.56–1.25, 18H, m, 4×CH$_3$, 3×CH$_2$.

100 MHz $^{13}$C-NMR (DMSO-d$_6$): 172.57; 172.39; 163.87; 155.18; C=O, 135.12; 125.52; C=C, 78.12; C$_q$-Boc; 63.43; 30.63; CH$_2$-bromoethyl ester; 62.95; CH$_2$-croton.; 48.92; CH-Ala; 38.87; 33.22; 28.62; 25.75; 24.04; CH$_2$; 28.08; CH$_3$-Boc; 16.84; CH$_3$-Ala.

EXAMPLE 9

N-tert.-Butyloxycarbonylalanyloxy-4-crotonyl-6-amidocaproic acid (viii)

The "C-terminal handle" is obtained analogously to the process described in Example 7 by cleavage of the corresponding bromoethyl ester (vii). Already after 9 hours, the thin layer chromatogram shows a complete reaction to a uniform product. After working up by acidic and alkaline shaking up analogously to Examples 7 and 4, respectively, there is obtained, in a yield of 53% of theory, the C-terminal free compound in the form of a yellowish oil which, already like the bromoethyl ester, precipitates out in the form of colourless crystals upon the addition of diethyl ether/petroleum ether.

$C_{18}H_{30}O_7N_2$ (386.4456)

Elementary analysis calc.: C 55.94%; H 7.82%; N 7.24%; found: 55.83%; 7.87%; 7.35%; Rf value: 0.20 (EE); Melting point: 71°–76° C. $[\alpha]_D^{22} = -17.64$ (c=1, methanol)

400 MHz $^1$H-NMR (DMSO-d$_6$): 11.99, 1H, s, COOH; 8.05, 1H, t, NH-capr., J=5.4 Hz; 7.31, 1H, d, NH-Ala, J=7.3 Hz; 6.60–6.53, 1H, m, CH=, J$_{trans}$=15.5 Hz, J$_{cis}$=9.7 Hz, J=1.6 Hz; 6.05–6.03, m, 1H, m, CH=, J=4.8 Hz; 4.75–4.64, 2H, m, CH$_2$-crot.; 4.05, 1H, dd, CH-Ala, J=7.3 Hz; 3.17–3.05, 2H, m, CH$_2$, J=6.1 Hz; J=6.7 Hz; 2.19–2.15, 2H, m, CH$_2$, J=7.4 Hz; 1.51–1.19, 18H, m, 4×CH$_3$, 3×CH$_2$.

100 MHz $^{13}$C-NMR (DMSO-d$_6$): 174.33; 172.64; 163.95; 155.25, C=O, 135.21, 125.59; C=C; 78.17; C$_q$-Boc; 62.98; CH$_2$-crotonic acid; 48.95; CH-Ala; 38.36; 33.53; 28.71; 25.93; 24.14; CH$_2$; 28.10; CH$_3$-Boc; 16.85; CH$_3$-Ala.

EXAMPLE 10

Synthesis of the N-protected pentapeptide Z-Val-Ala-Leu-Gly-Ala-OH

This is prepared with the use of the "handles" from Examples 7 and 9 and splitting off of the peptide from the carrier resin.

The synthesis of the pentapeptide takes place under standardised conditions with a peptide synthesiser PSS 80 of the firm Applied Protein Technics.

The individual reaction steps are as follows: In each case, 489 mg. p-aminomethylpolystyrene with the loading of 1.7 mmole NH$_2$/g. of resin (thus here corresponds to 0.84 mmole anchor groups) are suspended in 10 ml. of anhydrous dimethylformamide and mixed with the 4 fold molar amount of the corresponding "triple handle" (vi) and (viii), respectively (3.4 mmole), 4 mmole DIC and 4 mmole HOBt. After 25 minutes, the resin is washed with dimethylformamide and the coupling step is repeated. An internal monitoring examines the reaction. After the second coupling, a capping step takes place with acetic anhydride (20 minutes, 10 ml. 30% acetic anhydride in dimethylformamide). The reaction is subsequently examined by qualitative and quantitative amino acid sequence analysis. Subsequently, there takes place the splitting off of the Boc protective group with 20 ml. TFA/dichloromethane (1:1 v/v; 1 hour) and, after neutralisation and washing of the resin with triethylamine or dimethylformamide, the elongation of the peptide to the desired length. The coupling reagent is again DIC/HOBt and the Fmoc group is used as N-terminal protective group, in the case of valine the Z group. The molar excess is always four and coupling is carried out twice. The splitting off of the Fmoc protective group takes place throughout with piperidine and, in each case, the coupling period is 25 minutes. For the splitting off of the protective group, in each case 1 hour is necessary. After completion of the synthesis to give the N-terminal (Z)-protected pentapeptide, a quantitative and qualitative amino acid sequence analysis is carried out in order to monitor the synthesis and to obtain the loading of the resin with peptide. The β-alanine used as standard is thereby detected as phenylalanine (retention time: 46.883 minutes); capric acid is superimposed with histidine (the retention time is here 49.237 minutes).

The peptide is now split off from the polymeric carrier. For this purpose, the peptide-carrying resin (depending upon the reaction about 700 mg.) is introduced into anhydrous and oxygen-free tetrahydrofuran/dichloromethane/dimethyl sulphoxide (1:1:1 v/v/v), using argon as protective gas, three times the theoretical amount of morpholine are added thereto (referred to a quantitative reaction: 2.6 mmole) and mixed with a spatula tip of catalyst (tetrakis(triphenylphosphine)-palladium-(O) of the firm Janssen). Shaking is then carried out with the exclusion of light and oxygen for 12 hours, using argon as protective gas.

After completion of the cleavage reaction, the carrier resin is separated off and again washed three times with, in each case, 30 ml. tetrahydrofuran and methylene chloride. The solvent is removed by distillation from the combined organic filtrates and the residue is purified by column chromatography. The elution agent used is ethyl acetate/isopropanol/glacial acetic acid (12:1:0.1 v/v/v). There are finally obtained pale yellowish crystals.

Analytical data of the pentapeptide: $C_{27}H_{41}O_8N_5$ (563.648)

Amino acid sequence analysis (hydrochloric acid/propionic acid; 110° C., caproic acid as internal standard):

calc.: Gly=1; Ala=2; Leu=1; Val=1; found: Gly=1.2; Ala=1.85; Leu=1.09; Val=0.84.

Amino acid sequence analysis (hydrochloric acid/propionic acid; 110° C., β-alanine as internal standard):

calc.: Gly=1; Ala=2; Leu=1; Val=1; found: Gly=1.1; Ala=2.09; Leu=0.93; Val=0.9 Rf value: 0.62 (EE/isopropanol/HAc=12:1:0.1 v/v/v)

Melting point: 141°-144° C. $[\alpha]_D^{22}=0.31$ (c=1, methanol) 100 MHz $^{13}$C-NMR (DMSO-$d_6$)

Analysis data for the synthesis of the pentapeptide:

The loading of the resin was, in each case, determined by means of quantitative amino acid sequence analysis (conditions see above) and referred to the particular internal standard.

a) Internal standard β-alanine:

Loading of the resin with "triple handle": 0.6 mmole/g.; 36% amino acid sequence analysis after the synthesis to the dipeptide (resin-bound; Fmoc-Gly-Ala):

calc.: Gly=1; Ala=1; found: Gly=0.94; Ala=1.05. Loading of the resin with pentapeptide: 0.6 mmole/g.; 36%. Theoretically cleavable amount of peptide (489 mg. of resin were used): 169 mg. (0.3 mmole) Yield of peptide cleaved off: 142 mg. (0.25 mmole) Yield of peptide referred to the loading of the resin with "triple handle": 83%. Yield of peptide referred to the theoretically possible amount: 30%.

b) Internal standard 6-aminocaproic acid:

Loading of the resin with "triple handle": 1.1 mmole/g.; 65% Amino acid sequence analysis after the synthesis to the dipeptide (resin-bound; Fmoc-Gly-Ala):

calc.: Gly=1; Ala=1; found: Gly=0.97; Ala=1.2

Amino acid sequence analysis after the synthesis to the tetrapeptide (resin-bound; Fmoc-Ala-Leu-Gly-Ala):

calc.: Gly=1; Ala=2; Leu=1; found: Gly=1.09; Ala=1.77; Leu=1.13; Loading of the resin with pentapeptide: 1.1 mmole/g., 65%; Theoretically cleavable amount of peptide (489 g. of resin were used): 303 mg. (0.54 mmole); Yield of peptide cleaved off: 293 mg. (0.52 mmole) Yield of peptide referred to the loading of the resin with "triple handle": 97%. Yield of peptide referred to the theoretically possible amount: 62%.

We claim:

1. Process for the preparation of a solid phase system of the formula:

$$F-(-R^3-Y-CO-CR^2=CR^1-CH_2-X)_m \quad (II)$$

wherein
$R^1$ and $R^2$ which can be the same or different are hydrogen, halogen, $C_1$-$C_7$ alkyl or mono or dicyclic aryl,
$R^3$ is a linking group $(CH_2)_nCOOCH_2CH_2$ or $(CH_2)_n$ wherein n is 2-10,
X is acyloxy wherein the acyl is the residue of a $C_1$-$C_7$ aliphatic carboxylic acid or an N-protected amino acid or is RCO— wherein R is the protected or unprotected residue of an amino acid, peptide, glycopeptide, nucleotide, hydroxy carboxylic acid, dicarboxylic acid or tricarboxylic acid and
Y is oxygen, sulphur, or an —NH—,
A is a carboxylic acid ester group capable of reaction with a functional group B present on a solid carrier material selected from the group consisting of cross-linked polyacrylamides, methacrylates, dextrans, cellulose, polystyrene and cross-linked polystyrene,
F is a solid phase carrier material and m is the number of side chains bound to the carrier material comprising reacting an allyl ester of formula I:

$$X-CH_2-CR^1=CR^2-CO-Y-R^3-A \quad (I)$$

with a solid phase carrier-material F containing functional groups B wherein $R^1$, $R^2$, $R^3$, X and Y have the above meanings and wherein A and B react with one another to form a linkage between the solid phase carrier material F and X—CH$_2$—CR$^1$=CR$^2$—COY—R$^3$ comprising
reacting a compound of formula $$BrCH_2-CR^1=CR^2-COOOH_2CCl_3 \quad (2)$$

in which $R^1$ and $R^2$ have the above-given meanings, is reacted with a salt of an acid of the general formula XH (1), in which X has the above-given meaning, the so-obtained trichloroethyl ester of formula:

$$X-CH_2-CR^1=CR^2COOH_2Cl_3 \quad (3)$$

in which $R^1$, $R^2$ and X have the above-given meanings, is converted into the free acid of formula:

$$X-CH_2-CR^1=CR^2-COOH \quad (4)$$

in which $R^1$, $R^2$ and X have the above-given meanings, and this is reacted with a compound of formula:

$$HY-R^3-A \quad (5)$$

in which A, $R^3$ and Y have the above-given meanings, to give a compound of formula (I).

2. Process for the preparation of a solid phase system of formula:

$$F-(-R^3-Y-CO-CR^2=CR^1-CH_2-X)_m \quad (II)$$

wherein
$R^1$ and $R^2$ which can be the same or different are hydrogen, halogen, $C_1$-$C_7$ alkyl or mono or dicyclic aryl, $R^3$ is a linking group $(CH_2)_n COOCH_2CH_2$ or $(CH_2)_n$ wherein n is 2–10, X is acyloxy wherein the acyl is the residue of a $C_1$–$C_7$ aliphatic carboxylic acid or an N-protected amino acid or is RCO— wherein R is the protected or unprotected residue of an amino acid, peptide, glycopeptide, nucleotide, hydroxy carboxylic acid, dicarboxylic acid or tricarboxylic acid and Y is oxygen, sulphur, or an —NH—, A is a carboxylic acid ester group capable of reaction with a functional group B present on a solid carrier material selected from the group consisting of cross-linked polyacrylamides, methacrylates, dextrans, cellulose, polystyrene and cross-linked polystyrene, F is a solid phase carrier material and m is the number of side chains bound to the carrier material comprising reacting an allyl ester of formula I:

$$X-CH_2-CR^1=CR^2-CO-Y-R^3-A \qquad (I)$$

with a solid phase carrier-material F containing functional groups B wherein $R^1$, $R^2$, $R^3$, X and Y have the above meanings and wherein A and B react with one another to form a linkage between the solid phase carrier material F and X—CH$_2$—CR$^1$=CR$^2$—COY—R$^3$ comprising reacting a compound of the formula:

$$BrCH_2-CR^1=CR^2-COOH \qquad (6)$$

in which $R^1$ and $R^2$ have the above-given meanings with a compound of formula HY—R$^3$—A (5) to give a compound of the formula:

$$BrCH_2-CR^1=CR^2-CO-Y-R^3-A \qquad (7)$$

in which A, $R^1$, $R^2$ and Y have the above-given meanings, and converting compound (7) into a compound of formula (I) by reaction with a salt of an acid of general formula XH (1), in which X has the above meaning.

3. Process for the preparation of a solid phase system of the general formula:

$$F-(-R^3-Y-CO-CR^2=CR^1-CH_2-X)_m \qquad (II)$$

wherein $R^1$ and $R^2$ which can be the same or different are hydrogen, halogen, $C_1$–$C_7$ alkyl or mono or dicyclic aryl, $R^3$ is a linking group $(CH_2)_n COOCH_2CH_2$ or $(CH_2)_n$ wherein n is 2–10.

X is acyloxy wherein the acyl is the residue of a $C_1$–$C_7$ aliphatic carboxylic acid or an N-protected amino acid or is RCO— wherein R is the protected or unprotected residue of an amino acid, peptide, glycopeptide, nucleotide, hydroxy carboxylic acid, dicarboxylic acid or tricarboxylic acid and Y is oxygen, sulphur, or an —NH—, A is a carboxylic acid ester group capable of reaction with a functional group B present on a solid carrier material selected from the group consisting of cross-linked polyacrylamides, methacrylates, dextrans, cellulose, polystyrene and cross-linked polystyrene, F is a solid phase carrier material and m is the number of side chains bound to the carrier material comprising reacting an allyl ester of formula I:

$$X-CH_2-CR^1=CR^2-CO-Y-R^3-A \qquad (I)$$

with a solid phase carrier-material F containing functional groups B wherein $R^1$, $R^2$, $R^3$, X and Y have the above meanings and wherein A and B react with one another to form a linkage between the solid phase carrier material F and X—CH$_2$—CR$^1$=CR$^2$—COY—R$^3$ comprising reacting a compound of the formula:

$$BrCH_2-CR^1=CR^2-COOH \qquad (6)$$

with a compound of the formula:

$$HY-R^3-COO-CH_2-CH=CH_2 \qquad (8)$$

in which $R^3$ and Y have the above-given meanings, to give a compound of the formula:

$$BrCH_2-CR^1=CR^2-CO-Y-R^3-COO-CH_2-CH=CH_2 \qquad (9)$$

in which $R^1$, $R^2$, $R^3$ and Y have the above-given meanings, reacting the compound (9) with the salt of an acid of the formula XH (1), in which X has the above-given meaning, to give a compound of the formula:

$$X-CH_2-CR^1=CR^2-CO-Y-R^3-COO-CH_2-CH=CH_2 \qquad (10)$$

in which $R^1$, $R^2$, $R^3$, X and Y have the above-given meanings, and splitting off the allyl ester group thereby converting the compound (10) into a compound of the formula (I), wherein A is carboxyl group.

4. The method of claim 1, 2 or 3 wherein XH is an N-protected amino acid wherein the salt is a caesium salt.

5. Process according to any one of claims 1, 2 or 3, wherein the solid carrier material is a solid base material which is coated with a material appropriate for linking with allyl esters of general formula (I).

6. Process according to claim 5, wherein the solid phase, functional group B-containing carrier material F is an aminomethylated polystyrene or polyacrylamide which is reacted with an allyl ester of general formula (I) with the formation of an amide group.

* * * * *